United States Patent
Chandar et al.

(10) Patent No.: US 6,881,414 B2
(45) Date of Patent: Apr. 19, 2005

(54) MILD COSMETIC COMPOSITION WITH STABILIZED RETINOIDS

(75) Inventors: Prem Chandar, Closter, NJ (US); Quynh T. Pham, Murray Hill, NJ (US); Tak Yu Lam, Brooklyn, NY (US); Yan Zhou, Montville, NJ (US); Ritu Verma, New York, NY (US); Alexander Lips, Edgewater, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 63 days.

(21) Appl. No.: 09/998,958

(22) Filed: Nov. 1, 2001

(65) Prior Publication Data

US 2002/0110572 A1 Aug. 15, 2002

Related U.S. Application Data

(60) Provisional application No. 60/252,696, filed on Nov. 22, 2000.

(51) Int. Cl.$^7$ ............................. A61K 31/07; A61K 7/00
(52) U.S. Cl. .................... 424/401; 514/939; 514/938
(58) Field of Search .................... 424/401; 514/939, 514/169, 938

(56) References Cited

U.S. PATENT DOCUMENTS 6,346,256 B1 * 2/2002 Simon ...................... 424/401
6,482,397 B1 * 11/2002 Scott et al. .................. 424/59

FOREIGN PATENT DOCUMENTS

| EP | 0 421 333 | 4/1991 |
|----|-----------|--------|
| EP | 0 832 643 | 4/1998 |
| EP | 1 192 938 | 4/2002 |
| JP | 2000 44458 | 2/2000 |
| WO | 98/22084 | 5/1998 |
| WO | 99/20229 | 4/1999 |

OTHER PUBLICATIONS

J. C. Saari & D. L. Bredberg, "CoA and Non–CoA Dependent Retinol Esterification in Retinal Pigment Epithelium", J. Bill. Chem. 263, 8084–8090 (1988).

J. C. Saari & D. L. Bredberg, "ARAT & LRAT Activities of Bovine Retinal Pigment Epithelial Microsomes", Methods Enzymol. 190, 156–163 (1990).

J. L. Napoli & K. R. Race, "The Biosynthesis of Retinoic Acid from Retinol by Rat Tissues in vitro", Archives Biochem. Biophys. 255, 95–101 (1987).

R. Martini & M. Murray, "Participation of P450 3A Enzymes in Rat Hepatic Microsomal Retinoic Acid 4–Hydroxylation", Archives Biochem. Biophys. 303, 57–66 (1993).

A. B. Barua, "Analysis of Water–Soluble Compounds: Glucuronides", Methods Enzymol. 189, 136–145 (1990).

A. W. Norris and E. Li, "Generation and characterization of cellular retinoic acid–binding proteins from *Escherichia coli* expression systems." Methods Enzymol (1997).

Derwent Abstract of JP 2000 044458—published Feb. 15, 2000.

* cited by examiner

Primary Examiner—Sreeni Padmanabhan
Assistant Examiner—Shobha Kantamneni

(57) ABSTRACT

A cosmetic composition containing a retinoid and having an improved stability and mildness. Especially preferred compositions also include retinoid boosters and a polyhydric alcohol humectant.

5 Claims, No Drawings

MILD COSMETIC COMPOSITION WITH STABILIZED RETINOIDS

This application claims priority of application Ser. No. 60/252,696, filed Nov. 22, 2000.

FIELD OF THE INVENTION

The present invention relates to a cosmetic composition for skin and hair which deliver a retinoid, have improved retinoid stability and are also mild to the skin.

BACKGROUND OF THE INVENTION

Retinoids are known to provide a wide spectrum of skin benefits such as skin lightening, wrinkle treatment, oil control. Unfortunately, retinoids are unstable, , filed November especially in the presence of water. Cosmetic compositions, however, almost always include substantial amounts of water, in order to deliver an aesthetically acceptable appearance and tactile properties. Another drawback associated with the use of retinoids is their irritating potential, especially when applied in a relatively high concentration and/or applied to sensitive skin. Thus, cosmetic compositions that contain a retinoid of improved stability and which are also mild to the skin are commercially desirable.

SUMMARY OF THE INVENTION

A cosmetic oil-in-water emulsion composition including:
(a) a retinoid solubilized in a fluid oil,
(b) a polymeric emulsifier.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

The term "skin" as used herein includes the skin on the face, neck, chest, back, arms, hands, legs and scalp.

Retinoid Solubilized in a Fluid Oil

The inventive compositions contain a retinoid. Suitable retinoids include but are not limited to retinyl esters, retinol, retinal and retinoic acid, preferably retinol or retinyl ester. The term "retinol" includes the following isomers of retinol: all-trans-retinol, 13-cis-retinol, 11-cis-retinol, 9-cis-retinol, 3,4-didehydro-retinol, 3,4-didehydro-13-cis-retinol; 3,4-didehydro-11-cis-retinol; 3,4-didehydro-9-cis-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are $C_1$–$C_{30}$ esters of retinol, preferably $C_2$–$C_{20}$ esters, and most preferably $C_2$, $C_3$, and $C_{16}$ esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecanoate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, retinyl oleate.

The preferred ester for use in the present invention is selected from retinyl palmitate, retinyl acetate and retinyl propionate, because these are the most commercially available and therefore the cheapest. Retinyl linoleate and retinyl oleate are also preferred due to their efficacy.

The retinoid is employed in the inventive composition in an amount of at least about 0.001%, preferably from about 0.001% to about 10%, more preferably in an amount of from about 0.01% to about 1%, most preferably in an amount of from about 0.01% to about 0.5%.

The retinoid present in the inventive composition is solubilized in a fluid oil in order to improve the storage stability of the retinoid. Suitable fluid oils are selected in such a manner that the retinoid is soluble in an amount of at least 0.1 gram of retinoid per 100 grams of the oil at 25° C. Preferably retinoid is soluble in an amount of at least 2 grams of the retinoid per 100 grams of the oil, most preferably 2–80 grams of the retinoid per 100 grams of the oil.

As an illustration, solubility of retinol crystals in varying oils is as follows:

| Oil | Solubility, wt % |
| --- | --- |
| Mineral oil | 34.2 |
| Cetiol OE | 80 |
| Isostearyl palmitate | 44 |
| C12–15 Alkyl benzoate | 85 |
| Triolein/Squalene (6:1) | 56.4 |
| Cyclomethicone | 2.7 |
| Dimethicone | 0.49 |

Retinoid solubility in oil is determined by the following procedure. A known weight of pure retinoid in excess of the expected solubility limit in the oil is added in an oil. Methanol is added to the mixture to dissolve all retinoid crystals. Nitrogen sparging is used to ensure all methanol was evaporated from the oil. Retinoid is allowed to recrystallize overnight. The sample is filtered through a 0.45 micron filter. Known dilutions of the filtrate in isopropanol are measured by UV spectroscopy at an appropriate wavelength (325 nm for retinol) and the concentration of retinoid determined against calibration standards of retinoid in isopropanol.

Suitable fluid oils include but are not limited to esters of fatty acids or alcohols and hydrocarbons, preferably monoesters of fatty acids or alcohols, as long as they satisfy the solubility requirements described herein. Most preferably, fluid oil is selected from the group consisting of isostearyl palmitate, tridecyl salicylate, $C_{12-15}$ octanoate, isopropyl stearate, isopropyl myristate and isopropyl palmitate, or any mixtures thereof. Dicapryl ether, such as with a trade name Cetiol OE, is also included as most preferable oil.

Silicone oils may be also included in the compositions. These are preferably chosen from cyclic or linear polydimethylsiloxanes containing from about 3 to about 9, preferably from about 4 to about 5, silicon atoms. Other silicone oils may be also included, such as polyalkyl siloxanes, polyalkylaryl siloxanes and polyether siloxane copolymers (e.g. dimethicone copolyol). The polyalkyl siloxanes useful herein include, for example, polydimethyl siloxanes with viscosities of from about 5 to about 100,000 centistokes at 25° C., preferably, polydimethyl siloxanes having viscosities from about 10 to about 400 centistokes at 25° C.

The oils may be employed singly or in mixtures with one another.

The oil is employed in such an amount as to dissolve the selected amount of a retinoid and yet to not compromise the pleasing tactile properties of the inventive compositions.

Polymeric Emulsifier

The inventive compositions employ polymeric emulsifiers, in order to improve stability of retinoids in the compositions. Polymeric emulsifiers minimize the diffusion of water into an oil phase and thus minimize retinoid's exposure to water, which leads to an improved stability of retinoid.

Suitable polymeric wetting agents generally fall within the following two classes:
  (b1) an amphipathic block copolymer;
  (b2) a polymer containing a hydrophilic backbone modified with hydrophobic groups.

The block copolymers can be either diblocks (AB architecture) or triblocks (ABA or BAB architectures). For illustration, the A block is hydrophilic, e.g. polyethylene oxide, polyacrylamide, polyacrylic acid, siloxane, guar, and biopolymers (gum arabic, protein, gelatin). The B block is hydrophobic, e.g. polypropylene oxide, polyisobutalene, and polystyrene.

For hydrophobically modified polymers, the main component or backbone is hydrophilic. Along this backbone and/or at the terminal ends, hydrophobic groups (e.g. alkanes (C12 to C30)) are grafted. These polymers are produced by BASF, Rohm and Haas, BF Goodrich, etc., under the category of polymeric emulsifiers. For instance:
  BASF (Pluracares)
  B.F. Goodrich (Pemulens, Carbopol 1382)
  Rohm and Haas (Aculyn 22)
  Whitco (Silwet)

These molecules are predominantly hydrophilic and can be solubilized in a polar solvent (water, glycerol). However, the polymers also contain hydrophobic domains that allow the polymers to solubilize in non-polar or organic phases such as oil.

The polymeric emulsifier is included in the inventive compositions in the concentration of about 0.01% to about 10%, preferably about 0.1% to 2%, most preferably in order to minimize usage amount, about 0.1% to about 0.5%. The most preferred polymeric emulsifiers are Pemulen TR1, Pemulen TR2, Aculyn 22, and Pluracares, because these are cosmetically acceptable and efficient.

Preferably, the inventive compositions are substantially free of traditional emulsifiers such as sodium stearoyl lactylate, PEG-100 stearate, and ceteareth. Generally, the amount of traditional emulsifiers in the inventive compositions is less than 2%, preferably less than 1%, most preferably less than 0.5%. If used at all, preferably nonionic emulsifiers such as tween, are employed.

Stability of the Compositions

The inventive compositions exhibit substantially improved stability of the retinoid in the composition. Specifically, the half-life of the retinoid in the compositions is preferably at least about 20 days at 50° C., more preferably at least about 40 days at 50° C., most preferably at least about 70 days at 50° C.

Determination of Retinoid Half-life

"Half-life" is defined as the time it takes for retinoid to degrade to half of its original concentration at a given temperature.

Formulations are placed in an oven at 50° C. for an accelerated stability study. Retinoid is analyzed on time intervals for stability evaluation by an HPLC method described below. The studies showed that retinoid degradation followed a first order kinetics. Therefore, to determine the reaction half lifetime, the natural logarithm of remaining retinoid concentration is plotted against storage time to obtain a straight line with a slope k. The slope k is the rate of retinoid oxidation in reciprocal unit of time. The half lifetime of retinol is then determined by the ratio ln2/k.

The Procedure of Retinoid HPLC Analysis

A Waters Millipore system with Millennium32 software and with a photodiode array detector is used to collect the HPLC data. The chromatographic conditions are as follows:

| | |
|---|---|
| Column: | Phenonaenex I nertsil 5$\mu$ ODS 2 150 × 4.60 mm |
| Flow rate: | 1.0 mL/min |
| Injection volume: | 30 $\mu$L |
| UV detection: | 325 nm with Photodiode Array |
| Mobile phase: | 90/10 methanol/water |
| Run time: | 15 min |
| Temperature: | 4° C. |
| Retention time: | ca. 8.7 min. |

In order to prepare the sample solution to have a final retinoid concentration within the standard curve range, less than 10 ppm, 0.2 g cream sample is mixed with 2.5 g water first and vortexed to form a slurry. Then, methanol is added to the slurry to obtain a final total weight of 50 ml and vortexed again. The sample is subsequently filtered using a disposable syringe fitted with a 0.45 $\mu$m filter. All samples are prepared in triplicate for HPLC analysis.

Humectant

The humectant is preferably included in the inventive compositions to deliver a moisturizing benefit to the skin. Suitable humectants are polyhydric alcohols and include, but are not limited to glycerol (a.k.a. glycerine), humectants other than glycerine which can be added herein include (sorbitol, propylene glycol, butylene glycol, hexylene glycol, ethoxylated glucose and hexantriol). The humectant is included in the inventive compositions at a concentration of at least 10%. Preferably the concentration of at least 2% generally in the range of about 2% to about 90%. Preferably, about 5% to about 60%, most preferably, to optimize the moisturizer benefits, about 10% to about 35%. The most preferred humectants are glycerol and sorbitol—cosmetically preferred, low cost, and high efficacy.

Elastomer

An elastomer is a preferred optional ingredient for inclusion in the inventive compositions. Elastomers impart silkiness. These materials are blends of highly crosslinked siloxane polymers and silicone oils. Supplier sources include GE Silicones (Waterford, N.Y.), Dow Corning (Midland, Mich.), and Rhodia Silicones (Cranbury, N.J.). Elastomers are preferably included in an amount of about 0% to about 30%, preferably about 1% to about 15%, most preferably about 1% to about 10%. Most preferably, to help disperse elastomer and for skin lubricity the elastomer is included in combination with additional volatile silicone oils (cyclomethicones and dimethicones). In that case, the volatile silicone oil is included in an amount of about 0% to about 25%, preferably about 1% to about 10%.

Examples of Suitable Elastomers

| Trade Name | Source | CTFA Name | Ingredients |
|---|---|---|---|
| Silicone Elastomer Dispersion SFE839 | GE Silicones (Waterford, NY) | cyclopenta-siloxane and dimethicone/vinyl dimethicone crosspolymer | decamethyl cyclopenta siloxane, polydimethyl siloxane, octamethyl-cyclotetra siloxane, and mixed cyclosiloxanes |
| Silicone Elastomer Blend 9040 | Dow Corning (Midland, MI) | cyclomethicone and dimethicone crosspolymer | decamethyl cyclopenta siloxane, dimethyl methylalkenyl siloxane, and dimethyl cyclo-siloxanes |
| Rhodorsil Fluids 47 | Rhodia Silicones (Cranbury, NJ) | polydimethyl-siloxane | polydimethyl-siloxanes |

Retinoid Booster

The preferred compositions according to the invention comprise a retinoid booster.

It is believed that retinol esters and retinol are enzymatically converted in the skin into retinoic acid according to the following mechanism:

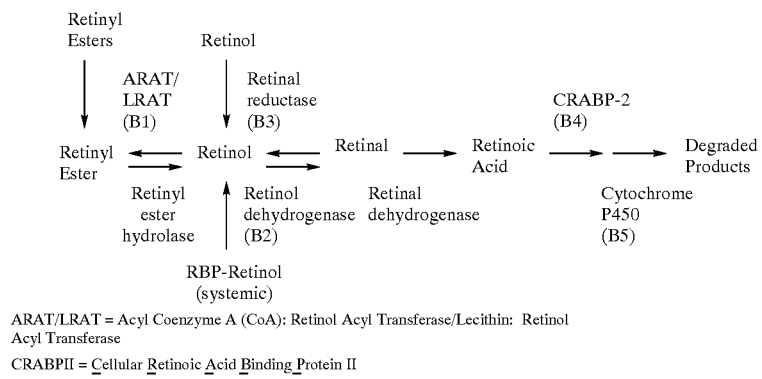

ARAT/LRAT = Acyl Coenzyme A (CoA): Retinol Acyl Transferase/Lecithin: Retinol Acyl Transferase
CRABPII = Cellular Retinoic Acid Binding Protein II Certain compounds inhibit ARAT/LRAT, retinal reductase, CRABPII and retinoic acid oxidation (the latter catalyzed by cytochrome P450 systems), whereas certain other compounds enhance retinal dehydrogenase. The compounds are collectively termed herein as "boosters" and are coded as groups B1 through B5 on the chart above. The boosters, alone or in combination with each other, potentiate the action of retinoid by increasing the amount of retinol available for conversion to retinoic acid and inhibiting the degradation of retinoic acid. The boosters act in conjunction with a retinoid (e.g. retinol, retinyl ester, retinal, retinoic acid).

The inventive compositions preferably contain about 0.0001% to about 50%, preferably about 0.001% to about 10%, most preferably about 0.001% to about 5% by weight of the composition of a booster or combination of boosters.

The boosters or combinations thereof included in the inventive compositions are selected from the group consisting of:
(a) a booster selected from the group consisting of B1, B2; B3; B4, B5;
(b) binary combinations of boosters selected from the group consisting of B1/B2; B1/B3; B1/B4; B1/B5; B2/B3, B2/B4; B2/B5, B3/B4; B3/B5; B4/B5;
(c) ternary combinations of boosters selected from the group consisting of B1/B2/B3; B1/B2/B4; B1/B2/B5; B1/B3/B4; B1/B3/B5; B1/B4/B5;B2/B3/B4; B2/B3/B5; B2/B4/B5; B3/B4/B5;
(d) quaternary combinations of boosters selected from the group consisting of B1/B2/B3/B4; B1/B2/B3/B5; B1/B2/B4/B5; B1/B3/B4/B5; B2/B3/B4/B5; and
(e) a combination of five groups of boosters: B1/B2/B3/B4/B5.

The compounds included in the present invention as boosters are selected based on the ability of such compounds to pass, at a certain concentration listed in Table A, an in-vitro Microsomal Assay for a specific enzyme as described below under sections 2.1 through 2.7. Such a booster is included in the present invention even if it is not explicitly mentioned herein. Put another way, if a compound inhibits or enhances sufficiently an enzyme in an assay described below, it will act in combination with a retinoid to mimic the effect on keratinocytes (skin cells) of retinoic acid, and thus it is included within the scope of the present invention.

By virtue of including a retinoid and, preferably, a retinoid booster, the inventive compositions are useful in prevention and treatment of dry skin, acne, photodamaged skin, appearance of wrinkles, age spots, aged skin, increasing stratum corneum flexibility, lightening skin color, controlling sebum excretion and generally increasing the quality of skin. The composition may be used to improve skin desquamation and epidermal differentiation.

The presence of the boosters in the inventive product substantially improves the performance of a retinoid.

The booster is a compound which passes an in vitro Microsomal Assay described below in sections 2.1 through 2.7. A compound suitable for use in the present invention inhibits or enhances at a concentration listed in Table A, an enzyme, to at least a broad % listed in Table A.

TABLE A

Booster Test Concentrations and % Inhibition/Increase

ARAT/LRAT Assay
(To identify B1 boosters)

| Invention | Compound Concentration | % Inhibition |
|---|---|---|
| Broad | 100 μM | >10% |
| Preferred | 100 μM | >25% |
| Most Preferred | 100 μM | >40% |
| Optimum | 100 μM | >50% |

Retinol Dehydrogenase Assay
(To identify B2 boosters)

| Invention | Compound Concentration | % Increase |
|---|---|---|
| Broad | 100 μM | >10% |
| Preferred | 100 μM | >15% |
| Most Preferred | 100 μM | >20% |
| Optimum | 100 μM | >25% |

Retinal Reductase Assay
(To identify B3 boosters)

| Invention | Compound Concentration | % Inhibition |
|---|---|---|
| Broad | 100 μM | >5% |
| Preferred | 100 μM | >10% |
| Most Preferred | 100 μM | >20% |
| Optimum | 100 μM | >35% |

CRABPII Antagonist Assay
(To identify B4 boosters)

| Invention | Compound:Retinoic acid Ratio | % Inhibition |
|---|---|---|
| Broad | 7000:1 | >25% |
| Preferred | 7000:1 | >50% |
| Most Preferred | 70:1 | >25% |
| Optimum | 70:1 | >50% |

Retinoic Acid Oxidation Assay
(To identify B5 boosters)

| Invention | Compound Concentration | % Inhibition |
|---|---|---|
| Broad | 100 μM | >25% |
| Preferred | 100 μM | >45% |
| Most Preferred | 100 μM | >70% |
| Optimum | 100 μM | >80% |

The in vitro Microsomal Assays employed for determining the suitability of the inclusion of the compound in the inventive compositions are as follows:

1. Materials

All-trans-retinol, all-trans-retinoic acid, palmitoyl-CoA, dilauroyl phosphatidyl choline, NAD, and NADPH were purchased from Sigma Chemical Company. Stock solutions of retinoids for the microsomal assays were made up in HPLC grade acetonitrile. All retinoid standard stock solutions for HPLC analysis were prepared in ethanol, stored under atmosphere of $N_2$ at −70° C. and maintained on ice under amber lighting when out of storage. Other chemicals and the inhibitors were commercially available from cosmetic material suppliers or chemical companies such as Aldrich or International Flavors and Fragrances.

2. Methods 2.1 Isolation of RPE microsomes (modified from J. C. Saari & D. L. Bredberg, "CoA and Non-CoA Dependent Retinol Esterification in Retinal Pigment Epithelium", *J. Bill. Chem.* 263, 8084–8090 (1988)).

50 frozen hemisected bovine eyecups, with the retina and aqueous humor removed were obtained from W. L. Lawson Co., Lincoln, Nebr., U.S.A. The eyes were thawed overnight and the colored iridescent membrane was removed by peeling with forceps. Each eyecup was washed with 2×0.5 mL cold buffer (0.1M $PO_4$/1 mM DTT/0.25M sucrose, pH 7) by rubbing the darkly pigmented cells with an artist's brush or a rubber policeman. The cell suspension was added to the iridescent membranes and the suspension was stirred for several minutes in a beaker with a Teflon stir bar. The suspension was filtered through a coarse filter (Spectra/Por 925 μl pore size polyethylene mesh) to remove large particles, and the resulting darkly colored suspension was homogenized using a Glas-Col with a motor driven Teflon homogenizer. The cell homogenate was centrifuged for 30 min. at 20,000 g (Sorvaal model RC-5B centrifuge with an SS34 rotor in 2.5×10 cm tubes at 14,000 RPM). The resulting supernatant was subjected to further centrifugation for 60 min. at 150,000 g (Beckman model L80 Ultracentrifuge with an SW50.1 rotor in 13×51 mm tubes at 40,000 RPM). The resulting pellets were dispersed into ~5 mL 0.1M $PO_4$/5 mM DTT, pH 7 buffer using a Heat Systems Ultrasonics, Inc. model W185D Sonifier Cell Disruptor, and the resulting microsomal dispersion was aliquoted into small tubes and stored at −70° C. The protein concentrations of the microsomes were determined using the BioRad Dye binding assay, using BSA as a standard.

2.2 Isolation of rat liver microsomes (R. Martini & M. Murray, "Participation of P450 3A Enzymes in Rat Hepatic Microsomal Retinoic Acid 4-Hydroxylation", *Archives Biochem. Biophys.* 303, 57–66 (1993)).

Approximately 6 grams of frozen rat liver (obtained from Harlan Sprague Dawley rats from Accurate Chemical and Scientific Corp.) were homogenized in 3 volumes of 0.1M tris/0.1M KCl/1 mM EDTA/0.25M sucrose, pH 7.4 buffer using a Brinkmann Polytron. The resulting tissue suspension was further homogenized in the motor driven Teflon homogenizer described above. The resulting homogenate was successively centrifuged for 30 min. at 10,000 g, 30 min. at 20,000 g, and 15 min. at 30,000 g, and the resulting supernatant was ultracentrifuged for 80 min. at 105,000 g. The pellet was sonicated in ~5 mL of 0.1M P04/0.1 mM EDTA/5 mM $MgCl_2$, pH 7.4 buffer as described above and stored as aliquots at −70° C. Protein concentrations were determined as described above.

2.3 Assay for ARAT and LRAT Activity (To Identify B1)

The procedure below is a modification of a method described in J. C. Saari & D. L. Bredberg, "ARAT & LRAT Activities of Bovine Retinal Pigment Epithelial Microsomes", *Methods Enzymol.* 190,156–163 (1990). The following buffer was prepared and stored at 4° C.: 0.1M $PO_4$/5 mM dithiothreitol, pH 7.0 ($PO_4$/DTT). On the day of the assay, add 2 mg BSA per mL of buffer to give a $PO_4$/DTT/BSA working buffer. 1 mM retinol substrate was prepared in acetonitrile and stored in amber bottles under nitrogen gas at −20° C. Solutions of 4 mM Palmitoyl-CoA in working buffer (stored in aliquots) and 4 mM dilauroyl phosphatidyl choline in ethanol were prepared and stored at −20° C. Inhibitors were prepared as 10 mM stock solutions in water, ethanol, acetonitrile or DMSO. The quench solution was prepared using pure ethanol containing 50 μg/mL butylated hydroxytoluene (BHT), and a hexane solution containing 50 μg/mL BHT was used for the extractions.

To a 2 dram glass vial, add the following in order: $PO_4$/DTT/BSA buffer to give a total volume of 500 μL, 5 μL acyl donor (4 mM palmitoyl-CoA and/or dilauroyl phosphatidyl choline), 5 μL inhibitor or solvent blank (10 mM stock or further dilutions) followed by approximately 15 μg of RPE microsomal protein (approximately 15 μL of a ~1 mg/mL microsomal protein aliquot). Incubate for 5 min. at 37° C. to equilibrate the reaction temperature and then add 5 μl 1 mM retinol. Cap the vials, vortex for 5 seconds and incubate for 30–90 minutes at 37° C. Quench the reaction by adding 0.5 mL ethanol/BHT. Extract the retinoids by adding 3 mL hexane/BHT, vortex the tubes for several seconds several times and centrifuge the tubes at low speed for 5 min. to quickly separate the layers. Remove the upper hexane layer into a clean vial, and re-extract the aqueous layer with another 3 mL hexane/BHT, as described above. Combine the hexane layers and evaporate the hexane by drying at 37° C. under a stream of nitrogen gas on a heated aluminum block. Store the dried residue at −20° C. until HPLC analysis. Quantitate the amount of retinyl palmitate and retinyl laurate for ARAT and LRAT activity, respectively, by integration of the HPLC signal as described below.

Note that the incubation solution contains 40 μM acyl donor, 100 μM or less inhibitor, 10 μM retinol, approximately 30 μg/mL microsomal protein, and nearly 0.1M PO$_4$, pH 7/5 mM DTT/2 mg/mL BSA. All steps subsequent to the addition of retinol were done in the dark or under amber lights.

2.4 Assay for Retinol Dehydrogenase Activity (To Identify B2)

The following stock solutions were prepared:
50 mM KH$_2$PO$_4$, pH 7.4 buffer, sterile filtered.
10 mM all trans Retinol (Sigma R7632) in DMSO.
200 mM Nicotinamide adenine dinucleotide phosphate, sodium salt (NADP) (Sigma N0505) in sterile water.
40 mM test compound in appropriate solvent (water, buffer, ethanol, chloroform or DMSO).
1:10 dilution of rat liver Microsomes in 50 mM KH$_2$PO$_4$, pH 7.4 buffer (4 micro g/micro l).

In a two-dram glass vial with screw cap, add the following in order:
Buffer to give a final volume of 400 μl
25 μl diluted Microsomes (final=100 μg)—use boiled Microsomes for controls and regular Microsomes for test samples.
4 μl of 200 mM NADP (final=2 mM)
1 micro l of 40 mM test compound (final=100 μM)
8 μl of 10 mM retinol (final=200 μM)

Incubate vials in a 37° C. shaking water bath for 45 minutes. Add 500 μl ice-cold ethanol to each vial to quench the reaction. Extract the retinoids twice with ice cold hexane (2.7 ml per extraction). Retinyl acetate (5 μl of a 900 μM stock) is added to each vial during the first extraction as a means of monitoring the extraction efficiency in each sample. Samples were vortexed for ten seconds before gently centrifuging for five minutes at 1000 rpm, 5° C. in a Beckman GS-6R centrifuge. The top hexane layer containing the retinoids is removed from the aqueous layer after each extraction to a clean two-dram vial. Evaporate off the hexane under a gentle stream of nitrogen gas. Store the dried residue at −20° C. until HPLC analysis.

2.5 Assay for Retinal Reductase Activity (To Identify B3)

All stock solutions were prepared as above with the following substitutions:
10 mM all trans Retinaldehyde (Sigma R2500) in DMSO—instead of retinol.
200 mM, Nicotinamide adenine dinucleotide phosphate, reduced form, tetrasodium salt (NADPH) (Sigma N7505) in sterile water—instead of NADP.

In a two-dram glass vial with screw cap, add the following in order:
Buffer to give a final volume of 400 μl
25 μl diluted Microsomes (final=100 μg)—use boiled Microsomes for controls and regular Microsomes for test samples.
4 μl of 200 mM NADPH (final=2 mM)
1 μl of 40 mM test compound (final=100 μM)
3 μl of 10 mM retinaldehyde (final=75 μM)
Follow the same incubation and extraction procedure as detailed above.

2.6 Assay for CRABPII Antagonists (To Identify B4)

2.6.1. Synthesis of CRABPII a. System of Expression

The gene CRABPII was cloned in pET 29a–c(+) plasmid (Novagen). The cloned gene was under control of strong bacteriophage T7 transcription and translation signals. The source of T7 polymerase was provided by the host cell *E.coli* BLR(DE3)pLysS (Novagen). The latter has a chromosomal copy of T7 polymerase under lacUV5 control, induced by the presence of IPTG.

The plasmid was transferred into *E. coli* BLR(DE3)pLysS cells by transformation according to the manufacturer protocol (Novagen).

b. Induction

An overnight culture of the transformed cells was diluted 1:100 into 2×YT containing 50 μg/mL kanamycin and 25 μg/mL chloramphenicol. The cells grew while shaking at 37° C. until the OD at 600 nm reached 0.6–0.8. Then IPTG was added to a final concentration of 1 mM and the culture was incubated for an additional two hours. The cells were harvested by centrifugation at 5000 g for 10 minutes at room temperature. The pellet was stored at −20° C.

2.6.2. Purification

Purification was performed according to the method described in A. W. Norris & E. Li, Generation and characterization of cellular retinoic acid-binding proteins from *Escherichia coli* expression systems". *Methods Enzymol.* 282:3–13 (1997).

a. Lysis

The frozen pellet was thawed at RT and resuspended in 1–2 pellet volumes of freshly prepared lysis buffer (50 mM Tris-HCl, pH 8, 10% (w/v) sucrose, 1 mM EDTA, 0.05% (w/v) sodium azide, 0.5 mM DTT, 10 mM MnCl$_2$, 2.5 mM phenylmethylsulfonyl fluoride, 2.5 mM benzamidine, 6 μg/mL DNase). The lysate was incubated for 30 min at room temperature. Further lysis was accomplished by sonication (six 30-sec bursts at 10,000 psi alternated with five 30-sec delay on ice). The insoluble fraction of the lysate was removed by centrifugation at 15000 rpm 1 hour at 4° C. and the supernatant is stored at −20° C.

b. Gel filtration on Sephacryl S300

The supernatant from step a. was loaded onto a 2.5×100 cm column of sephacryl S-300 (Pharmacia) at room temperature. The elution buffer was 20 mM Tris-HCl, pH 8, 0.5 mM DTT, 0.05% sodium azide (buffer A). The flow rate was 2 mL/min. Collected 2-mL fractions were checked for ultraviolet absorbance at 280 nm. The fractions representing the peaks were examined by SDS-page for the presence of CRABPII.

c. Anion-Exchange Chromatography 2 mL of gel filtration fractions containing CRABPII were loaded onto a quaternary amine anion-exchange column FPLC (Fast Protein Liquid Chromatography) type monoQ (Pharmacia). CRABPII was eluted using a gradient buffer from 100% buffer A to 30% buffer B (100% buffer B=buffer A+250 mM NaCl) over a 20-min period at room temperature. 1 mL-fractions were collected every minute. Once more, the presence of CRABPII was checked by SDS page. CRABPII was stored at 4° C. before freeze-drying using a Micromodulyo 1.5K with vial platform attachment (Edwards High Vacuum International). The desiccated samples were stored at room temperature until their use in the binding assay.

d. Detection of the Presence of CRABPII

The expression and purification of CRABPII was validated using denaturing SDS-polyacrylamide gel electrophoresis (SDS-PAGE) analysis on a 7–15% polyacrylamide gel (Biorad). 10 µL samples were mixed with 10 µL of 2× loading buffer (100 mM Tris-HCl pH6.8, 4% SDS, 0.2% BPB, 20% glycerol, 1 mM DTT) and denatured by heating (2 min at 80° C.). The samples were loaded onto the gel that was immersed in a 1× Tris-glycine buffer (Biorad) and a constant current (25 mA) was applied for 1 hour at room temperature. After Coomassie blue staining, the protein was identified according to its molecular weight as determined with the Benchmark prestained protein ladder (Gibco BRL).

A western blot was used to confirm the presence of CRABPII. The proteins separated on the SDS-PAGE were transferred on an Immobilon-P transfer membrane (Millipore) using a Biorad cassette. The transfer occurred in 1× Tris-glycine buffer (Biorad) +10% methanol. An electrical current (60 mA) was applied for 3 hours to allow the protein to migrate through the membrane. Afterwards, the membrane was blocked with 5% dry milk in 1×TBS for one hour at room temperature and probed with primary antibodies to CRABPII (1/1000 dilution of mouse anticlonal 5-CRA-B3) in the same buffer at 4° C. overnight. The following day, the membrane was washed with PBS (3×5 minutes) and then incubated with 1:2000 dilution of the secondary antibody, peroxidase conjugated anti-mouse antibody (ECLTM, Amersham), for 1 hour at room temperature. The membrane was washed with 1×PBS (3×5 minutes) and the protein was detected using ECL detection kit according to the manufacturer instruction (Amersham).

The concentration of purified CRABPII was determined using BSA kit (Pierce).

2.6.3. Radioactive Binding Assay 220 pmol of CRABPII was incubated in 20 mM Tris-HCl buffer pH 7.4 with 15 pmol of radioactive all trans retinoic acid (NEN) in a total volume of 70 µL. For the competitive assay, another ligand in excess (6670:1, 670:1 or 70:1) was added to the mix. The reaction occurred for one hour at room temperature in the dark. In order to separate the unbound all-trans retinoic acid from the bound all-trans retinoic acid, a 6 kD cut-off minichromatography column (Biorad) was used. The storage buffer was discarded using a Microplex manifold according to the manufacturer instruction (Pharmacia). The samples were loaded onto the column and the separation occured by gravity over a 30-min period. Retinoic acid ("RA") bound to CRABPII appeared in the filtrate while free RA remained in the column. The radioactivity of the filtrate was measured by scintillation counter.

2.7 Assay for NADPH Dependent Retinoic Acid Oxidation (To Identify B5)

The procedure below is a modification of a method described in R. Martini & M. Murray, "Participation of P450 3A Enzymes in Rat Hepatic Microsomal Retinoic Acid 4-Hydroxylation", *Archives Biochem. Biophys.* 303, 57–66 (1993). Prepare the following assay buffer and store at 4° C.: 0.1M $PO_4$/0.1 mM EDTA/5 mM $MgCl_2$, pH 7.4. On the day of the assay, prepare a 60 mM NADPH solution in buffer. Prepare inhibitor stocks, acidified ethanol/BHT quench solution, and hexane/BHT as described above. A working 1 mM retinoic acid solution was prepared by dilution of a 15 mM stock (in DMSO) with ethanol.

To a 2 dram vial, add the following in order: assay buffer to give a final volume of 500 µL, 20 µL 60 mM NADPH, 5 µL inhibitor or solvent blank, followed by approximately 2 mg of rat liver microsomal protein. Incubate for 5 min. at 37° C., then add 5 µL working 1 mM retinoic acid solution.

Continue incubation for 60 min. at 37° C.—do not cap the vials, since the oxidation process requires molecular oxygen in addition to NADPH. Quench with acidified ethanol/BHT and extract with hexane/BHT as described above. Quantitate the quickly eluting polar retinoic acid metabolites (presumed to be 4-oxo retinoic acid) by integration of the HPLC signal, as described below.

Note that all steps subsequent to the addition of retinoic acid were done in the dark or under amber lights. The final incubation solution contains 2.4 mM NADPH, 100 µM or less inhibitor, 10 µM retinoic acid, approximately 4 mg/mL rat liver microsomal protein and nearly 0.1M $PO_4$/0.1 mM EDTA/5 mM $MgCl_2$.

HPLC Analysis of Individual Retinoids

Samples for retinoid quantitation by HPLC were prepared by dissolving the residue in each vial with 100 µL of methanol. The solution was transferred to a 150 µL glass conical tube within a 1 mL shell vial, capped tightly, and placed inside a Waters 715 Autosampler. Aliquots of 60 µL were injected immediately and analyzed for retinoid content.

The chromatography instrumentation consisted of a Waters 600 gradient controller/pump, a Waters 996 Photodiode Array detector and a Waters 474 Scanning Fluorescence detector. Two HPLC protocols were used for retinoid analysis. For the ARAT and LRAT assay, the separation of retinol and retinol esters was performed with a Waters 3.9×300 mm C18 Novapak reverse-phase analytical column and Waters Sentry NovaPak C18 guard column with an 80:20(v/v) methanol/THF isocratic mobile phase adjusted to a flow rate of 1 mL/min. for 10 min. The eluate was monitored for absorbance at 325 nm and fluorescence at 325ex/480em. A shorter Waters 3.9×150 mm C18 Novapak reverse-phase analytical column and Waters Sentry Nova-Pak C18 guard column were used to separate retinoid acids and alcohols for the retinol and retinoic acid oxidation assays utilizing a modification of a gradient system described by A. B. Barua, "Analysis of Water-Soluble Compounds: Gluconomides", *Methods Enzymol.* 189, 136–145 (1990). This system consisted of a 20 min. linear gradient from 68:32(v/v) methanol/water containing 10 mM ammonium acetate to 4:1(v/v) methanol:dichloromethane followed by a 5 min. hold at a flow rate of 1 mL/min. The column eluate was monitored from 300 nm to 400 nm.

These protocols were selected based on their ability to clearly resolve pertinent retinoid acids, alcohols, aldehydes, and/or esters for each assay and relative quickness of separation. Identification of individual retinoids by HPLC was based on an exact match of the retention time of unknown peaks with that of available authentic retinoid standards and UV spectra analysis (300–400 nm) of unknown peaks against available authentic retinoids.

The boosters suitable for use in the present invention include but are not limited to the boosters listed in Tables B1 through B5 below.

| | | ARAT/LRAT Inhibitors (B1) | | | | | |
|---|---|---|---|---|---|---|---|
| Class | Compound | % Inhibition Overall TG (- ROH/RE) | Overall TG (IC 50) | % Inhibition ARAT (10 μm) | % Inhibition ARAT (100 μm) | % Inhibition LRAT (10 μm) | % Inhibition LRAT (100 μm) |
| Carotenoid | Crocetin | | 3.75E-05 | 15% | 34% | 0 | 15% |
| Fatty Acid Amides & Other Surfactants | Acetyl Sphingosine | | 6.78E-06 | 19% +/- 12 | 62% +/- 11 | 10% +/- 10 | 50% +/- 18 |
| Fatty Acid Amides & Other Surfactants | C13 Beta-Hydroxy Acid/Amide | 17% | | | 28% | | 25% |
| Fatty Acid Amides & Other Surfactants | Castor Oil MEA | | 3.25E-05 | | | | |
| Fatty Acid Amides & Other Surfactants | Cocamidopropyl Betaine | | | | 25% | | |
| Fatty Acid Amides & Other Surfactants | Coco Hydroxyethylimidazoline | | 2.84E-07 | | 68% | | 68% |
| Fatty Acid Amides & Other Surfactants | Cocoamide-MEA (or Cocoyl Monoethanolamide) | 11% | | | 13% | | 34% |
| Fatty Acid Amides & Other Surfactants | Glycerol-PCA-Oleate | | | | 41% +/- 6 | | 58% +/- 2 |
| Fatty Acid Amides & Other Surfactants | Hexanoamide | | | | 20% | | |
| Fatty Acid Amides & Other Surfactants | Hexanoyl Sphingosine | | 9.99E-05 | | 28% +/- 4 | | 37% +/- 9 |
| Fatty Acid Amides & Other Surfactants | Hydroxyethyl-2-Hydroxy-C12 Amide | | 3.29E-05 | | 35% | | 35% |
| Fatty Acid Amides & Other Surfactants | Hydroxyethyl-2-Hydroxy-C16 Amide | | | | 25% | | 30% |
| Fatty Acid Amides & Other Surfactants | Lauroyl Sarcosine | | | | 20% | | |
| Fatty Acid Amides & Other Surfactants | Lidocaine | | | | 12% | | 0 |
| Fatty Acid Amides & Other Surfactants | Linoleamide-DEA (or Linoleoyl Diethanolamide) | 59% | | 12% +/- 13 | 43% +/- 3 | 11% +/- 9 | 51% +/- 15 |
| Fatty Acid Amides & Other Surfactants | Linoleamide-MEA (or Linoleoyl Monoethanolamide) | | 1.61E-05 | 14% | 35% | 20% +/- 8 | 35% |
| Fatty Acid Amides & Other Surfactans | Linoleamidopropyl Dimethylamine | | | | 69% +/- 18 | | 75% +/- 4 |
| Fatty Acid Amides & Other Surfactants | Melinamide | | | | 64% +/- 15 | | 43% +/2 21 |
| Fatty Acid Amides & Other Surfactans | Myristoyl Sarcosine | | | | 41% +/- 14 | | 11% +/- 11 |
| Fatty Acid Amides & Other Surfactants | Oleyl Betaine | | 2.80E-05 | | 47% | | |
| Fatty Acid Amides & Other Surfactants | Palmitamide-MEA | | | 6% | 23% | 12% | 33% |
| Fatty Acid Amides & Other Surfactants | Stearylhydroxyamide | | | | 10% | | 10% |
| Fatty Acid Amides & Other Surfactants | Utrecht-1 | 21% | | 43% | 54% | 51% | 48% +/- 6 |
| Fatty Acid Amides & Other Surfactants | Utrecht-2 | | 3.47E-06 | 42% | 83% +/- 9 | 51% | 92% +/- 3 |
| Flavanoids | Naringenin | | | | 33% | | 14% |
| Fragrances | Allyl Alpha-Ionone | | | 16% +/- 14 | 22% +/- 23 | 17% +/- 10 | 36% +/- 7 |
| Fragrances | Alpha-Damascone | | 3.35E-04 | 67% +/- 27 | 83% +/- 12 | 87% +/- 6 | 98% +/- 1 |
| Fragrances | Alpha = Ionone | | 9.27E-04 | | 45% +/- 27 | | 49% +/- 30 |
| Fragrances | Alpha-Methyl Ionone | | | | 67% | | 77% |
| Fragrances | Alpha-Terpineol | | | | 26% | | 25% |
| Fragrances | Beta-Damascone | | | 45% | 84% | 52% | 92% |
| Fragrances | Brahmanol | | | | 70% | | 75% |
| Fragrances | Damascenone | | | 23% | 70% | 29% | 79% |
| Fragrances | Delta-Damascone | | | 58% | 87% | 64% | 95% |
| Fragrances | Dihydro Alpha-Ionone | | | | 13% | | 18% |
| Fragrances | Ethyl Saffranate | | | | 51% | | 49% |
| Fragrances | Fenchyl Alcohol | | | | 12% | | 4% |
| Fragrances | Gamma-Methyl Ionone | | | | 21% | | 38% |
| Fragrances | Isobutyl Ionone | | | | 8% | | 45% |
| Fragrances | Isocyclogeraniol | | | | 18% | | 16% |
| Fragrances | Isodamascone | | | | 80% | | 92% |
| Fragrances | Lyral | | 1.27E-04 | | 76% | | 71% |
| Fragrances | Santalone | | | | 23% | | 12% |
| Fragrances | Santanol | | | | 15% | | 43% |
| Fragrances | Timberol | | | | 34% | | 33% |
| Fragrances | Tonalid | | | | 50% | | 33% |
| Fragrances | Traseolide | | | | 41% | | 21% |
| Miscellaneous | Coca Trimethylammonium Cl- | | | | 27% | | |
| Miscellaneous | Urosolic Acid | | 1.46E-06 | | 21% | | 28% |
| Noncyclic Fragrances | Citral | | | | 20% | | |

ARAT/LRAT Inhibitors (B1)

| Class | Compound | % Inhibition Overall TG (- ROH/RE) | Overall TG (IC 50) | % Inhibition ARAT (10 μm) | % Inhibition ARAT (100 μm) | % Inhibition LRAT (10 μm) | % Inhibition LRAT (100 μm) |
|---|---|---|---|---|---|---|---|
| Noncyclic Fragrances | Citronellol | | | | 30% | | 0 |
| Noncyclic Fragrances | Farnesol | | 9.35E−05 | 23% +/− 18 | 53% +/− 18 | 10% +/− 7 | 53% +/− 19 |
| Noncyclic Fragrances | Geraniol | | 7.83E−03 | 13% | 32% | | |
| Noncyclic Fragrances | Geranyl Geraniol | | | 38% +/− 12 | 81% +/− 6 | 16% +/− 9 | 77% +/− 13 |
| Noncyclic Fragrances | Linatool | | | | 28% | | 0 |
| Noncyclic Fragrances | Nonadieneal | | | | 20% | | |
| Noncyclic Fragrances | Pseudoionone | | | | 12% | | 37% |
| Phospholipid | Dioctylphosphatidyl Ethanolamine | | | 23% | 50% +/− 2 | 0 | 17% +/− 17 |
| Urea | Dimethyl Imidazolidinone | 22% | | | | | |
| Urea | Imidazolidinyl Urea | 35% | | | | | |

Retinol Dehydrogenase Activators (B2)

| Class | Compound | % Increase Retinol Dehydrogenase |
|---|---|---|
| Phospholipid | Phosphatidyl Choline | 21% increase |
| Phospholipid | Sphingomyelin | 26% increase |

Retinaldehyde Reductase Inhibitors (B3)

| Class | Compound | Overall TG (IC 50) | % Inhibition Retinal Reductase |
|---|---|---|---|
| Miscellaneous | Carbenoxolone | 3.61E−07 | 26% +/− 2 |
| Miscellaneous | Glycyrretinic Acid | 8.64E−06 | 38% =/− 1 |
| Phospholipid | Phosphatidyl ethanolamine | | 37% |
| Aldehyde | Vanillin | 9.70E−03 | 6% |
| Fatty Acid | Arachidic Acid | | 20% |
| Fatty Acid | Arachidic Acid | | 49% |
| Fatty Acid | Linoleic Acid | 1.63E−04 | 62% +/− 2 |
| Fatty Acid | Linolenic Acid | 1.34E−04 | 54% +/− 16 |
| Fatty Acid | Myristic Acid | 1.72E−05 | 26% |
| Miscellaneous | Amsacrine | 6.26E−06 | 22% +/− 8 |

CRABPII Antagnoists (B4)

| Class | Compound | Overall TG (IC 50) | % Inhibition CRABPII |
|---|---|---|---|
| Fatty Acid | Elaidic Acid | 6.50E−05 | >50% |
| Fatty Acid | Hexadecanedioic Acid | 1.30E−04 | >50% |
| Fatty Acid | 12-Hydroxystearic Acid | 2.91E−05 | >50% |
| Fatty Acid | Isostearic Acid | 6.88E−05 | >50% |
| Fatty Acids | Linseed Oil | | >50% |

Retinoic Acid Oxidation Inhibitors (B5)

| Class | Compound | Overall TG (IC 50) | % Inhibition Retinoic Acid (10 μM) | % Inhibition Retinoic Acid (100 μM) |
|---|---|---|---|---|
| Imidazole | Bifonazole | | 89% | 100% |
| Imidazole | Climbazole | 4.47E−06 | 80% | 92% |
| Imidazole | Clotrimazole | | 76% | 85% |
| Imidazole | Econazole | | 88% | 100% |
| Imidazole | Ketoconazole | 1.85E−07 | 84% | 84% |
| Imidazole | Miconazole | 2.78E−07 | 74% | 86% |
| Fatty Acid Amides & Other Sufactants | Lauryl Hydroxyethylimidazoline | 4.67E−07 | | |
| Fatty Acid Amides & Other Sufactants | Oleyl Hydroxyethylimidazoline | 3.02E−05 | 54% | 80% |
| Flavanoids | Quercetin | 6.29E−05 | 40% | 74% |
| Coumarin | Coumarin | | | |
| Quinoline | (7H-Benzimidazo[2,1-a]Benz[de]-Isoquinolin-7-one | 8.59E−07 | | |
| Quinoline | Hydroxyquinoline (Carbostyril) | 3.64E−07 | | |
| Quinoline | Metyrapone (2-Methyl-1, 2-di-3-Pyridyl-1-Propane | | | 47% |

The preferred boosters or combinations thereof inhibit transglutaminase (hereinafter "Tgase") in a transglutaminase assay described below to at least 50% at a concentration of 10 mM.

TGase Assay

| Invention | Compound Concentration | % Inhibition |
|---|---|---|
| Broad | 10 mM | >50% |
| Preferred | 1 mM | >50% |
| Most Preferred | 100 µM | >50% |
| Optimum | 10 µM | >50% |

Transglutaminase Assay
Transglutaminase Assay and Keratinocyte Differentiation

During the process of terminal differentiation in the epidermis, a 15 nm thick layer of protein, known as the cornified envelope (CE) is formed on the inner surface of the cell periphery. The CE is composed of numerous distinct proteins which have been cross-linked together by the formation of $N^\epsilon$-($\gamma$-glutamyl) lysine isodipeptide bonds catalyzed by the action of at least two different transglutaminases (TGases) expressed in the epidermis. TGase I is expressed in abundance in the differentiated layers of the epidermis, especially the granular layer, but is absent in the undifferentiated basal epidermis. Thus TGase I is a useful marker of epidermal keratinocyte differentiation with high TGase I levels indicating a more differentiated state. An ELISA based TGase I assay, using a TGase I antibody, was used to assess the state of differentiation of the cultured keratinocytes in the examples that follow.

Keratinocytes (cultured as described above) were plated in 96 well plates at a density of 4,000–5,000 cells per well in 200 µl media. After incubation for two to three days, or until cells are ~50% confluent, the media was changed to media containing test compounds (five replicates per test). The cells were cultured for a further 96 hours after which time the media was aspirated and the plates stored at −70° C. Plates were removed from the freezer, and the cells were washed twice with 200 µl of 1×PBS. The cells were incubated for one hour at room temperature (RIT) with TBS/5% BSA (wash buffer, bovine serum albumin). Next the TGase primary antibody was added: 50 µl of monoclonal anti-Tgase I Ab B.C. diluted 1:2000 in wash buffer. The primary antibody was incubated for 2 hours at 37° C. and then rinsed 6× with wash buffer. Cells were then incubated with 50 µl of secondary antibody (Fab fragment, peroxidase conjugated anti-mouse IgG obtaining from Amersham) diluted 1:4,000 in wash buffer for two hours at 37° C., then rinsed three times with wash buffer. Following the rinse with washing buffer, the cells were rinsed 3× with PBS. For colourimetric development, the cells were incubated with 100 µl substrate solution (4 mg o-phenylenediamine and 3.3 µl 30% $H_2O_2$ in 10 ml 0.1M citrate buffer pH 5.0) for exactly five minutes, R/T, in darkness (under aluminum foil). The reaction was stopped by the addition of 50 µl 4N $H_2SO_4$. The absorbance of samples was read at 492 nm in a 96 well plate UV spectrophotometer. Out of the five replicates, four were treated with both antibodies, the fifth one was use as a Tgase background control. TGase levels were determined and expressed as percentage control.

Transglutaminase levels were determined and expressed in the Tables B1 through B5 above either as:
(i) % (booster+retinol inhibition/control inhibition)−% (ROH inhibition/control inhibition), which measures the added effect of booster+retinol induced TGase inhibition over retinol alone, or (ii) as an IC50 value when the inhibitory effect of multiple booster concentrations was examined–this provides the concentration of booster which, in combination with a constant retinol concentration of $10^{-7}$M, inhibits TGase by 50%.

Best Groups of Boosters

| B1 Compounds | | |
|---|---|---|
| 1. | Fatty Acid Amides | These are readily commercially available and have the added advantage of being surfactants and thus help generate emulsions suitable for cosmetic preparations. |
| 2. | Ceramides | These can additionally act as precursors of stratum corneum barrier ceramides. |
| 3. | Carotenoids | These can offer some UV protection and and act as natural colorants. |
| 4. | Flavanoids | Natural antioxidants. |
| 5. | Cyclic fragrances | These are readily commercially available and additionally can be used to fragrance the product. |
| 6. | Non-cyclic fragrances | These can be used to fragrance the product. |
| 7. | Phospholipid analogues | These can be utilised by skin cells to nourish the generation of barrier components. |
| 8. | Ureas | These are readily commercially available and can also act as preservatives for the product. |

| B2 Compounds | |
|---|---|
| 1. Phosphatidyl choline | Most preferred as most active activator of Retinol Dehydrogenase |
| 2. Sphingomyelin | |

| B3 Compounds | |
|---|---|
| Arachidonic Acid | Fatty Acids which can be useful in maintaining stratum corneum barrier |
| Linoleic Acid | |
| Linolenic Acid | |
| Myristic Acid | |
| Linoleic Acid | Essential Fatty Acids |
| Linolenic Acid | |
| Arachidonic Acid | Non-essential fatty acids |
| Myristic Acid | |
| Glycyrrhetinic Acid | Polycyclic triterpene carboxylic acid which is readily obtained from plant sources. |
| Phosphatidyl ethanolamine | Can be incorporated into cellular membranes. |

| B4 Compounds | |
|---|---|
| Hexadecanedioic acid | Saturated fatty acids. |
| 12-hydroxystearic acid | |
| Isostearic acid | |
| Linseed oil | Unsaturated fatty acids |
| Elaidic acid | |
| Elaidic acid | Solid at room temperature |
| Isostearic acid | |
| Hexadecanedioic acid | |
| Linseed oil | Liquid at room temperature |
| 12-hydroxystearic acid | |

| | B5 Compounds |
|---|---|
| Bifonazole | Antimicotics |
| Climbazole | |
| Clotrimazole | |
| Econazole | |
| Ketoconazole | |
| Miconazole | |
| Climbazole | Readily commercially available |
| Lauryl hydroxyethylimidazoline | Compounds which are readily commercially available and have the added advantage of being surfactants and thus help generate emulsions suitable for cosmetic preparations. |
| Quercetin | Naturally occuring flavanoid which has antioxidant properties. |
| Coumarin | Natural colorant |
| Quinolines | |
| Isoquinolines | |
| Metyrapone | |

Further Optional Ingredients

Crystalline Fatty Acid

The crystalline fatty acid is an optional ingredient. Preferably, the fatty acid contains from 12 to 22 carbon atoms, because such acids are cheap and the most aesthetically acceptable. The most preferred fatty acid is stearic acid. The term "acid" as employed herein does not exclude the presence of a salt of fatty acid depending on the pH of the final composition. For instance, sodium, potassium or ammonium salts may be present. The salt amount is included in the amount of fatty acid. The inventive compositions preferably contain at least 0% of fatty acid, most preferably from 0.1% to 18%.

The inventive compositions most preferably further include an ingredient selected from the group consisting of antioxidants, reducing agents, chelating agents, and mixtures thereof to improve the stability of a retinoid. These ingredients provide an additional level of protection against oxidation of retinoids. Common examples of antioxidants, reducing agents and chelating agent for the present formulations can be found in the CTFA International Cosmetic Ingredient Dictionary $4^{th}$ Edition, The Cosmetic, Toiletry, and Fragrance Association, Inc., Washington, D.C., 1991.

Preferable reducing agents are sodium sulfite, sodium bisulfite, sodium metabisulfite, sodium thiosulfite or other thiols, such as thioglycerol, thiourea, thioglycolic acid, cysteine and the like. Preferable antioxidants are rac-6-hydroxy-2,5,7,8-tetra-methylchromane-2-carboxylic acid (trolox), propyl gallate, n-propyl trihydroxybenzoate, t-butyl hydroquinone and butylated hydroxytoluene (BHT), butylated hydroxyanisole (BHA), tocopheryl acetate, ascorbyl palmitate, hydroquinone, dibutyl hydroquinone and the like.

Suitable examples of chelating agents include, but are not limited to, EDTA, citric acid, tartaric acid, organo aminophosphonic acids and organo phosphonic acid components including certain of the commercially available Dequest™ compounds, marketed by Monsanto. Preferred is 1-hydroxyethylene, (1.1-diphosphonic acid).

Organo aminophosphonic acid is an organic compound comprising of at least one phosphonic acid group, and at least one amino group. Suitable organo aminophosphonic acid components for use herein include the amino alkylene poly (alkylene phosphonic acids) and nitrilo trimethylene phosphonic acids. Examples of this type of organo aminophosphonic acid components include certain of the commercially available Dequest™ compounds, marketed by Monsanto.

Preferred are amino tri (methylene phosphonic acid) (Dequest 2006®), diethylene triamine penta (methylene phosphonic acid) and hexamethylene diamine tetra (methylene phosphonic acid).

Other suitable additional heavy metal ion sequestrants for use herein include nitrilotriacetic acid and polyaminocarboxylic acids such as ethylenediaminotetracetic acid, or ethylenetriamine pentacetic acid.

Still other suitable additional heavy metal ion sequestrants for use herein are iminodiacetic acid derivatives such as 2-hydroxyethyl diacetic acid or glyceryl imino diacetic acid.

Antioxidants are included in the inventive compositions in an amount of from 0.01 to 10%, preferably from 0.1 to 5%, most preferably from 0.2 to 4%. Reducing agents are included in the inventive compositions in an amount of from 0.01 to 10%, preferably from 0.1 to 5%, most preferably from 0.2 to 4%. Chelating agents are included in the inventive compositions in an amount of from 0.01 to 1%, preferably from 0.05 to 0.5%, most preferably from 0.05 to 0.3%.

The especially preferred compositions include 0.1% bisulfite, 0.7% Dequest 2006® and 0.2% BHT.

Various types of active ingredients may be present in cosmetic compositions of the present invention. Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens, skin lightening agents, tanning agents.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively.

The exact amount of sunscreen employed in the emulsions can vary depending upon the degree of protection desired from the sun's UV radiation.

Another preferred optional ingredient is selected from essential fatty acids (EFAs), i.e., those fatty acids which are essential for the plasma membrane formation of all cells, in keratinocytes EFA deficiency makes cells hyperproliferative. Supplementation of EFA corrects this. EFAs also enhance lipid biosynthesis of epidermis and provide lipids for the barrier formation of the epidermis. The essential fatty acids are preferably chosen from linoleic acid, γ-linolenic acid, homo-γ-linolenic acid, columbinic acid, eicosa-(n-6,9,13)-trienoic acid, arachidonic acid, γ-linolenic acid, timnodonic acid, hexaenoic acid and mixtures thereof.

Other optional ingredients may include coloring agents, opacifiers and pigments (e.g. titanium dioxide, silica) and perfumes. Amounts of these materials may range anywhere between 0.001% and 20% by weight of the composition.

Cosmetically Acceptable Vehicle

The composition according to the invention also comprises a cosmetically acceptable vehicle to act as a dilutant, dispersant or carrier for the active components in the composition, so as to facilitate their distribution when the composition is applied to the skin or hair.

Vehicles other than or in addition to water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition.

Use of the Composition

The composition according to the invention is intended primarily as a product for topical application to human skin or hair, especially as an agent for conditioning and smoothening the skin, and preventing or reducing the appearance of wrinkled or aged skin or dry hair.

In use, a small quantity of the composition, for example from 1 to 5 ml, is applied to exposed areas of the skin or hair, from a suitable container or applicator and, if necessary, it is then spread over and/or rubbed into the skin or hair using the hand or fingers or a suitable device.

Product Form and Packaging

The composition can be packaged in a suitable container to suit its viscosity and intended use by the consumer. For example, a composition can simply be stored in a non-deformable bottle or squeeze container, such as a tube or a lidded jar.

The invention accordingly also provides a closed container containing a cosmetically acceptable composition as herein defined.

The following specific examples further illustrate the invention, but the invention is not limited thereto.

EXAMPLES

1. All preparation performed at room temperature (20–25° C.) using overhead mixers (1000–2000 rpm)
2. Mix aqueous components (water, glycerol, Pemulen, and preservatives) together at 1000–1500 rpm until Pemulen is fully solvated.
3. In separate container, mix oils (silicone oil and/or other optional oils) and elastomer at 1000 rpm.
4. Add BHT and retinol to oil mixture in step #3; mix at 1000 rpm for 5–10 minutes.
5. Add aqueous phase from step #2 to oil phase from step #4, mix at 1000–1500 rpm for 5–10 minutes.
6. Add TEA last, mix at 1500–2000 rpm until well blended, 5–10 minutes.

Note: Anti-oxidants such as Dequest 2066, Na bisulfite, and Na2CO3 are added to the water phase in step #2. Transcutol is added to the oil phase in step #3.

B. Retinol Stability

Prototypes were stored in amber glass jars at 50° C. Aliquots were taken from the same jars at time=0, 1, 2, 3, 4, 6, 8, and 12 week for retinol stability measurement. Retinol stability was monitored using HPLC; each sample was analyzed in triplicates.

Sample prototypes with retinol stability data are shown in the following three tables. Table 1 details formulations with retinol in silicone oil. Table 2 details formulations with retinol in Cetiol oil. Table 3 details formulations with retinol in other oils.

TABLE 1

| Ingredient | Function | Phase | Example 1A | Example 1B | Example 1C |
|---|---|---|---|---|---|
| Water | | aqueous | 33.85 | 32.96 | 32.76 |
| Glydant DMDM hydantoin | preservative | aqueous | 0.50 | 0.50 | 0.50 |
| Glycerol | humectant | aqueous | 35.00 | 35.00 | 35.00 |
| Pemulen TR II | polymeric emulsifier | aqueous | 0.25 | 0.25 | 0.25 |
| TEA (triethylamine) | pH adjuster | aqueous | 0.30 | 0.30 | 0.30 |
| Elastomer GE 839 | silicone elastomer | oil | 25.00 | 25.00 | 25.00 |
| Silicone oil 245 | oil | oil | 5.00 | 5.00 | 5.00 |
| BHT (butylated hydroxytoluene) | anti-oxidant | oil | | 0.20 | 0.20 |
| Dequest 2006 (pentasodium aminotrimethylene phosphonate) | anti-oxidant | aqueous | | 0.49 | 0.49 |
| Sodium bisulfite | anti-oxidant | aqueous | | 0.20 | 0.20 |
| Retinol | active | oil | 0.20 | 0.20 | 0.20 |
| Sodium carbonate | pH adjuster | aqueous | | | 0.20 |

TABLE 2

| Ingredient | Function | Phase | Example 2A | Example 2B | Example 2C | Example 2D |
|---|---|---|---|---|---|---|
| Water | | aqueous | 33.85 | 32.96 | 32.66 | 31.66 |
| DMDM hydantoin | preservative | aqueous | 0.50 | 0.50 | 0.50 | 0.50 |
| Glycerol | humectant | aqueous | 35.00 | 35.00 | 35.00 | 35.00 |
| Pemulen TR II | polymeric emulsifier | aqueous | 0.25 | 0.25 | 0.25 | 0.25 |
| TEA (triethylamine) | pH adjuster | aqueous | 0.30 | 0.30 | 0.30 | 0.30 |
| Elastomer GE 839 | silicone elastomer | oil | 25.00 | 25.00 | 25.00 | 25.00 |
| Cetiol OE | oil | oil | 5.00 | 5.00 | 5.00 | 5.00 |
| Transcutol (ethoxydiglycol) | cosolvent | oil | | | | 1.00 |
| BHT (butylated hydroxytoluene) | anti-oxidant | oil | | 0.20 | 0.20 | 0.20 |
| Dequest 2006 (pentasodium aminotrimethylene phosphonate) | anti-oxidant | aqueous | | 0.49 | 0.49 | 0.49 |
| Sodium bisulfite | anti-oxidant | aqueous | | 0.20 | 0.20 | 0.20 |
| Retinol | active | oil | 0.20 | 0.20 | 0.20 | 0.20 |
| Sodium carbonate | pH adjuster | aqueous | | | 0.20 | 0.20 |

TABLE 3

| Ingredient | Function | Phase | Example 3A | Example 3B |
|---|---|---|---|---|
| Water | | aqueous | 33.85 | 36.66 |
| DMDM hydantoin | preservative | aqueous | 0.50 | 0.50 |
| Glycerol | humectant | aqueous | 35.00 | 35.00 |
| Pemulen TR II | polymeric emulsifier | aqueous | 0.25 | 0.25 |
| TEA (triethylamine) | pH adjuster | aqueous | 0.30 | 0.30 |
| Elastomer GE 839 | silicone elastomer | oil | 25.00 | 25.00 |
| Petrolatum | oil | oil | 5.00 | |
| Transcutol (ethoxydiglycol) | cosolvent | oil | | 1.00 |
| BHT (butylated hydroxytoluene) | anti-oxidant | oil | | 0.20 |
| Dequest 2006 (pentasodium aminotrimethylene phosphonate) | anti-oxidant | aqueous | | 0.49 |
| Sodium bisulfite | anti-oxidant | aqueous | | 0.20 |

TABLE 3-continued

| Ingredient | Function | Phase | Example 3A | Example 3B |
|---|---|---|---|---|
| Retinol | active | oil | 0.20 | 0.20 |
| Sodium carbonate | pH adjuster | aqueous | | 0.20 |

Retinol Stability at 50 C.

| Storage Time (days) at 50 C. | Retinol Remained at Percentage of Original | | | | | | | | |
|---|---|---|---|---|---|---|---|---|---|
| | 1A | 1B | 1C | 2A | 2B | 2C | 2D | 3A | 3B |
| 0 | 100 | 100 | 100 | 100 | 100 | 100 | 100 | 100 | 100 |
| 7 | 89.9 | 93.6 | 99.2 | 87.6 | 89.2 | 96.1 | 92.7 | 93.1 | 95.8 |
| 14 | 83.7 | 92 | 92.1 | 83.7 | 86.3 | 93.3 | 93.8 | 83.1 | 92.6 |
| 21 | 83.1 | 86.9 | 91.9 | 82.1 | 86.5 | 92.4 | 91.6 | 89.2 | 86.5 |
| 28 | 76.1 | 84.5 | 89.3 | 76.7 | 89 | | | 79.6 | 87.7 |
| 42 | | | 77.1 | | | 64.8 | | | 77.9 |
| 56 | 58 | 80.6 | 77.8 | 66.8 | 82.4 | 62.3 | | 65.9 | 77.3 |
| 84 | 45.6 | 72.8 | 65.8 | 58.5 | 49.2 | | | 52.9 | 70.8 |
| 168 | | 33.5 | 32.8 | 24.4 | 41.9 | 46.8 | 53.1 | 21 | 29.8 |
| t ½ (days) | 178 | 67 | 142 | 98 | 122 | 133 | 182 | 91 | 151 |

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as described and claimed herein, and that the inventions be limited only by the scope of the claims which follow, and that such claims be interpreted as broadly as is reasonable. Throughout this application, various publications have been cited. The entireties of each of these publications are hereby incorporated by reference herein.

What is claimed is:

1. A cosmetic oil-in-water emulsion composition consisting essentially of:
   (a) a retinoid solubilized in a fluid oil,
   (b) a polymeric emulsifier selected from polymers containing a hydrophilic backbone modified with hydrophobic groups and mixtures thereof, wherein the polymeric emulsifiers are selected from the group consisting of Pemulen TR1, Pemulen TR2, Aculyn 22, and Pluronic F68; and
   (c) about 1% to about 90% of a polyhydric alcohol humectant: wherein the half-life of the retinoid in the composition is at least about 70 days at 50° C.

2. The composition of claim 1 wherein the amount of retinoid is at least about 0.001% by weight of the composition.

3. The composition of claim 1 wherein the retinoid is selected from the group consisting of retinoic acid, retinol, retinyl esters, and retinal.

4. The composition of claim 1 wherein the retinoid is soluble in the fluid oil in an amount of at least about 0.1 g of the retinoid per about 100 g of the oil at 25° C.

5. The composition of claim 1, wherein said fluid oil is selected from the group consisting of esters of fatty acids, alcohols, hydrocarbons, and mixtures thereof.

* * * * *